United States Patent [19]
Prabhu

[11] Patent Number: 5,945,281
[45] Date of Patent: Aug. 31, 1999

[54] METHOD AND APPARATUS FOR DETERMINING AN ANALYTE FROM A SAMPLE FLUID

[75] Inventor: Ajoy K. Prabhu, Columbia, Md.

[73] Assignee: Becton, Dickinson and Company, Frankin Lakes, N.J.

[21] Appl. No.: 08/594,610

[22] Filed: Feb. 2, 1996

[51] Int. Cl.⁶ ........................................................ C12Q 1/68
[52] U.S. Cl. ................................ 435/6; 435/526; 435/525
[58] Field of Search .................................. 435/6, 526, 525

[56] References Cited

U.S. PATENT DOCUMENTS 5,279,936   1/1994   Vorpahl ........................................ 435/6

*Primary Examiner*—Scott W. Houtteman
*Attorney, Agent, or Firm*—Bruce S. Weintraub

[57] ABSTRACT

A device and system for assaying a target analyte from a sample fluid. According to the device, the target analyte is separated from the sample fluid through interaction with magnetic capture agents and application of an electromagnetic field. In this manner, fluid reagents used in the assay need not be transported or removed from the device when the assay is being conducted.

10 Claims, 4 Drawing Sheets ns by Technicon (now Miles
METHOD AND APPARATUS FOR DETERMINING AN ANALYTE FROM A SAMPLE FLUID

BACKGROUND OF THE INVENTION

1. Technical Field of the Invention

This invention relates to a method and apparatus for detecting a target analyte from a sample fluid. More specifically, the target analyte is separated from the sample fluid through interaction with magnetic capture agents, and application of an electromagnetic field transports the separated analyte for detection. In this manner, fluid reagents used in the assay need not be transported or removed from the device when the assay is being conducted.

2. Brief Description of the Related Technology

Specific binding assays have found wide-spread use in the detection of target analytes contained in sample fluids, particularly in the field of biomedical research. The target analytes which are detectable using such specific binding assays include hormones, vitamins, blood group antigens, viruses (e.g., rotavirus), microorganisms (e.g., Streptococcus, Salmonella, Treponema, and the like), therapeutic drugs (e.g., theophylline), abused drugs (e.g., canabinoids, morphine, and the like), and pesticides (e.g., arachor). In addition, the fields of forensic detection (e.g., animal vs. human blood), blood typing rare blood groups, and environmental monitoring (e.c., polychlorinated biphenyls) also benefit from such specific binding assays.

Specific binding assays are of two types: homogeneous specific binding assays and heterogeneous specific binding assays. Using either assay, a target analyte becomes bound to a capture agent thereby forming a complex and a detectable response from that complex is determined. In homogenous specific binding assays, the detectable response of unbound or free analytes differs from that of the analyte bound in the complex. Hence, the bound analyte can be distinguished from the unbound analyte and detection of the target analyte may be accomplished selectively without requiring physical separation of the bound analyte from the sample. See e.g., S.H. Jenkins, "Homogeneous Enzyme Immunoassay", *J. Immun. Meth.*, 150, 91–97 (1992).

In addition, homogeneous specific binding assays are relatively simple to perform and are easily adaptable to automated analyzers. Previous commercial analyzers that have been used in the clinical laboratory include the ACA™, a discrete analyzer from Du Pont de Nemours and Co., Wilmington, Del.; the SMAC™, an analyzer based on linear flow of analytes made by Technicon (now Miles Diagnostics, Tarrytown, N.Y.) and the Cobas™, which is an analyzer based on centrifugal forces which transport reagents and is available from Roche Diagnostics, Branchburg, N.J.

Such homogeneous specific binding assays do, however, require several intermediate steps, each of which typically includes the use of separate reagents. In addition, although the lack of a separation step is beneficial from an ease of performance standpoint, it is detrimental to the extent that the sensitivity and specificity of certain assays may be hindered. Sensitivity and specificity may be compromised due to the presence of background interference, the cause of which ordinarily would be removed during a separation step.

In contrast to homogeneous specific binding assays, heterogeneous specific binding assays exhibit identical responses from the bound analyte and the unbound analyte. A separation step is therefore required in order to obtain meaningful detection results. Once the bound analyte is separated from the unbound analyte, the heterogeneous specific binding assay demonstrates high sensitivity and analyte specificity. An example of such a heterogeneous specific binding assay is described in C. Tu et al., "Ultrasensitive Heterogeneous Immunoassay Using Photothermal Deflection Spectroscopy", *Anal. Chem.*, 65, 3651–53 (1993).

Previously, magnetic particles have been used in heterogeneous specific binding assays. In fact, they have been reported as useful for the separation and concentration of analytes from an analyte-containing sample, and particularly useful for the separation of unbound tag (or detector) reagents from analyte-bound tag (or detector) reagent. See e.g. U.S. Pat. No. 5,147,529 (Lee). To date, however, there has been no attempt to use magnetic particles in heterogeneous specific binding assays as both a capture agent to bind a target analyte and as a vehicle to move that bound analyte through various reagents and ultimately for detection. Rather, in the past (such as described in connection with the '529 patent) magnetic particles have been placed in a reservoir to bind an analyte, and exposure of an electromagnetic field thereto would cause the magnetic particles to aggregate along the portion of a wall of the reservoir at which the electromagnetic field was applied. By so doing, reagent removal and introduction was facilitated without removing the magnetic particles therefrom, and the assay was conducted with the magnetic particles remaining within the same reservoir.

In addition, Japanese Patent Document JP 43-23,559 is directed to an immunoassay for determining the amount of antigen in a sample using antibody-fixed magnets. These antibody-fixed magnets are said to be arranged so that they can be moved along the depth direction of the wall of a reaction vessel depending on the depth of liquid in the vessel.

Magnetic particles have also been used as precipitating reagents in assays. However, such a use of magnetic particles, like those uses discussed above, is not as a mobile phase for the assay.

It would be desirable for a heterogeneous specific binding assay to use magnetic particles for binding a target analyte in one portion of a device and through the use of an applied potential (which generates an electromagnetic field) to transport the analyte-bound magnetic particles out of that one portion of the device and into another portion of the device so as to render the bound analyte available for detection. And, for reasons of both manufacturing efficiency and health care cost reduction, it would be desirable to perform such heterogeneous specific binding assays in at least a semi-automated manner without compromising the quality or accuracy of the results obtained and the time required to properly conduct the assay.

SUMMARY OF THE INVENTION

The present invention meets the desires described above by providing a device for assaying a target analyte. The device comprises a housing which comprises a means for receiving a tray. The tray includes at least one well, in which is disposed a fluid containing a target analyte, a magnetic capture agent and a label, and a detection region. The device may also provide input means, such as an alphanumeric keypad, for inputting data to the device. Examples of data which may be input include the assay type, and information identifying the target analyte, the volume of the fluid, the label and the magnetic capture agent.

In addition, the device has a means for applying a wave-like electrical potential, such as a microprocessor. This potential transports a complex which forms of the target analyte, the magnetic capture agent and the label to the detection region of the tray. The device also has a detector for identifying the presence of the target analyte (in the complex) at the detection region.

The present invention also provides a tray comprising a body provided with a fluid-receiving well, an interconnection region and a detection region. The fluid-receiving well contains a magnetic capture agent and a label for binding to a target analyte.

The present invention further provides a process for assaying a target analyte. The process comprises the steps of selecting an assay tray provided with a magnetic capture agent and a label; adding to the assay tray a fluid sample; causing any target analyte in the fluid sample to form a complex with the magnetic capture agent and the label to facilitate identification of the presence of the target analyte; applying electrical potential to the complex and transporting the complex to a detection region; and determining the presence of the complex in the detection region.

The present invention avoids reagent cross-contamination in the assay by moving the bound analyte (and not the reagents, in liquid form) from one compartment to the next.

DETAILED DESCRIPTION OF THE INVENTION

The present invention will now be described in further detail with reference to the appended Figures.

Figure 1:
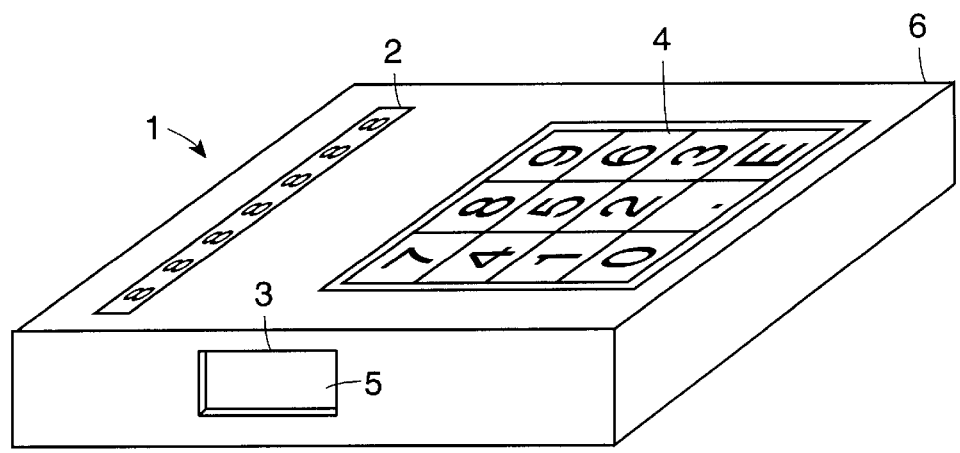
FIG. 1 is a perspective view of an analyzer in accordance with the present invention.

FIG. 1 depicts a perspective view of an analyzer 1 which includes a housing 6, along one side of which is provided a port 3 capable of receiving an assay tray 30 (described with reference to FIG. 3). When not in use, the entry port 3 remains sealed, for instance by pivoting or sliding retractable internal flap 5 as shown in FIG. 1. On the top of housing 6 is provided a liquid crystal display ("LCD") panel 2 for data readout and an alphanumeric keypad 4 for data entry.

Figure 3A:
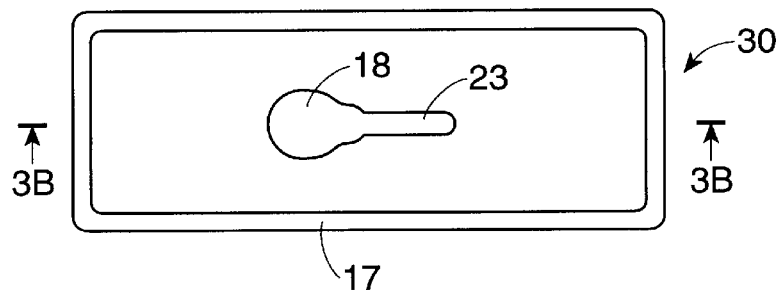
FIG. 3A is a top view of an assay tray for use with the analyzer of FIG. 1.
Figure 3B:
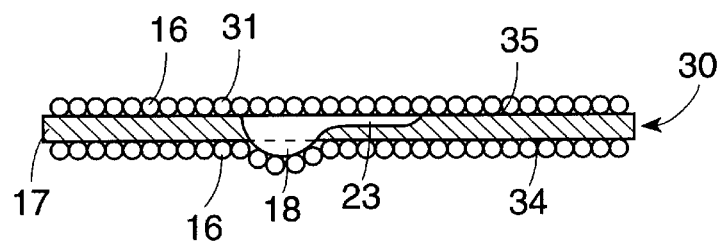
FIG. 3B is a cross-section of the assay tray depicted in FIG. 3A, taken generally along the line 3B—3B.

FIGS. 3A and 3B show an assay tray 30 according to this invention, which is useful for separating an analyte from a fluid sample for detection and analysis. Assay tray 30 is formed by an elongated body 17 which may be constructed from a variety of materials. Although there is no limitation on these materials, magnetically transparent materials such as nonmagnetic and nonferrous materials are preferred, especially plastic materials including thermoplastics (e.g., polyvinylchloride and polystyrene), thermosets, and the like.

Assay tray 30 may be fabricated in a variety of well-known conventional processes, including thermoforming, reaction injection molding, spin-molding, etc., with the fabrication method depending on the custom for the particular materials chosen for use.

Body 17 defines a well 18 for receiving sample and a detection region 23. When the sample is introduced to sample well 18, magnetic capture agents contained in sample well 18 form an analyte/capture agent complex with any analyte sought to be assayed (the "target analyte").

Thereafter, assay tray 30 is exposed to an electrical potential, which creates an electromagnetic field capable of transporting the analyte/capture agent complex from sample well 18 to analyte detection region 23 for analyte detection.

The magnetic capture agent is generally formed of two materials, namely a magnetic transport material and a material for capturing the analyte to be assayed. The capture agent itself may include any of a variety of materials capable of interacting with a particular target analyte in a fluid sample.

The type of interaction between the capture agent and the target analyte depends on the particular target analyte and the capture agent used. Such interactions include ionic bonding, covalent bonding, hydrogen bonding, bonding through van der Waals or electrostatic forces, and integration through steric incorporation. Specific examples of such interactions include antibody-antigen interaction, complementary nucleotide interaction, hormone-receptor interaction, and the like.

For instance, the capture agent may possess free basic or amino groups to interact with acidic groups in the target analyte, or the capture agent may possess free acidic groups to interact with basic or amino groups in the sample analyte. Through this interaction, the target analyte should become sufficiently associated with the capture agent so as to permit the magnetic material to transport the target analyte to detection region 23. In this regard, it is not required that the capture agent bind irreversibly or even strongly to the target analyte. However, in the event that the capture agent reversibly binds to the target analyte, it is desirable that sufficiently excess capture agent be utilized in order to ensure that essentially all target analyte is bound to magnetic capture agent at any given moment. This is especially so when the capture agent binds only weakly to the target analyte.

Desirably, a capture agent may be provided by a monoclonal or polyclonal antibody capable of interacting with and binding an antigen present only on the target analyte to form a complex therewith. One example of an antibody-antigen interaction is group A Streptococcus IgG antibody ("GAS IgG") for binding group A Streptococcus antigen ("GAS Ag"). Other examples of complexes include thyroid stimulating hormone ("TSH")/anti-TSH antibody complexes; human chorionic gonadotropin ("hcG")/anti-hcG antibody complexes; sense strand DNA or RNA/anti-sense strand DNA or RNA, respectively, complexes; protein A/IgG complexes; strepavidin or avidin/biotin complexes; and noble metal/sulfhydryl group complexes.

To prepare the magnetic capture agent, magnetic materials, preferably magnetic particles are caused to physically or chemically bind with the capture agent. For instance, a magnetic capture agent capable of associating with nucleic acids may be prepared from biotinylated bovine serum albumin ("biotin-BSA") (commercially available from Pierce, Rockford, Ill.) and magnetic particles. Unlike the binding between the target analyte and the capture agent, the binding between the magnetic materials and the capture agent should be strong and, if possible, effectively irreversible.

The magnetic particles may be composed of materials including iron beads, such as those having a particle size within the range of about 0.2μm to about 200μm, preferably 0.5 μm to 100 μm, especially 0.5 μm to 25 μm. Particularly suitable magnetic particles for use herein include 5% (w/v) suspension of magnetic particle having a particle size of about 0.9 μm (Sera-Mag ™ commercially available from Seradyne Corporation, Indianapolis, Ind.).

Of course, if the capture agent itself has sufficient magnetic properties (such as an antibody containing a magnetized heme group, for instance), it is not required that a magnetic particle be utilized. In some instances, if the target analyte has sufficient magnetic properties (such as a magnetized ferrous porphyrin, for instance) it may in fact be possible to omit use of both the capture agent as well as the magnetic particle.

Synthesis Example

A magnetic capture agent was prepared by incubating 200 μL of Sera-Mag™ suspended magnetic particles overnight at a temperature of about 4° C. with about 5 μg/mL of 0.3 M glycine at a pH of 9.6.

Thereafter, the incubated magnetic particles were washed twice with FTA (fluorescent trepanemal antibody) hemagglutination buffer (commercially available from Becton Dickinson Microbiology Systems, Sparks, Md.) at 20,000 rpm using a Beckman TL-100 ultracentrifuge (Beckman Corp., Palo Alto, Calif.).

Strepavidin (Bethesda Research Labs, Bethesda, Md.) was added to the washed particles, in an amount of about 50 μg/ml, to the hemagglutination buffer and incubated for about 1 hour at about 37° C.

After incubation, unbound strepavidin was separated from the mixture by centrifuging at about 20,000 rpm and removed, whereupon a blocking buffer (about 0.05% of BSA (w/v) in hemagglutination buffer) was added to the mixture and incubated for a period of time of about 30 minutes at about 37° C. This formed the magnetic capture agents, which were removed from the reaction mixture, washed twice in hemagglutination buffer at 20,000 rpm and resuspended in hemagglutination buffer for later use.

The method of the present invention involves introducing a target analyte to a magnetic capture agent within sample well 18 of the assay tray 30 to form a analyte/capture agent complex This occurs by adding a target analyte-containing fluid to sample well 18 which contains magnetic capture agent.

The binding of target analyte to magnetic capture agent is ordinarily carried out at a temperature within the range of about 20° to about 45° C., preferably about 37° C., and ordinarily occurs within a period of time of about 30 seconds to about five minutes, preferably about 30 seconds to about one minute. Of course, the reaction temperatures and times will necessarily vary within or beyond the above-recited parameters depending on the particular target analyte and the magnetic capture agent chosen to bind that analyte.

After the fluid sample is added to sample well 18, assay tray 30 is inserted via flap 5 past entry port 3 into analyzer 1 in order to (1) bind the target analyte to the magnetic capture agent and a detector reagent (or "label") (discussed in more detail below) and (2) transport the analyte/capture agent/detector reagent complex to detection region 23 by applying an electrical potential to assay tray 30.

Figure 2:
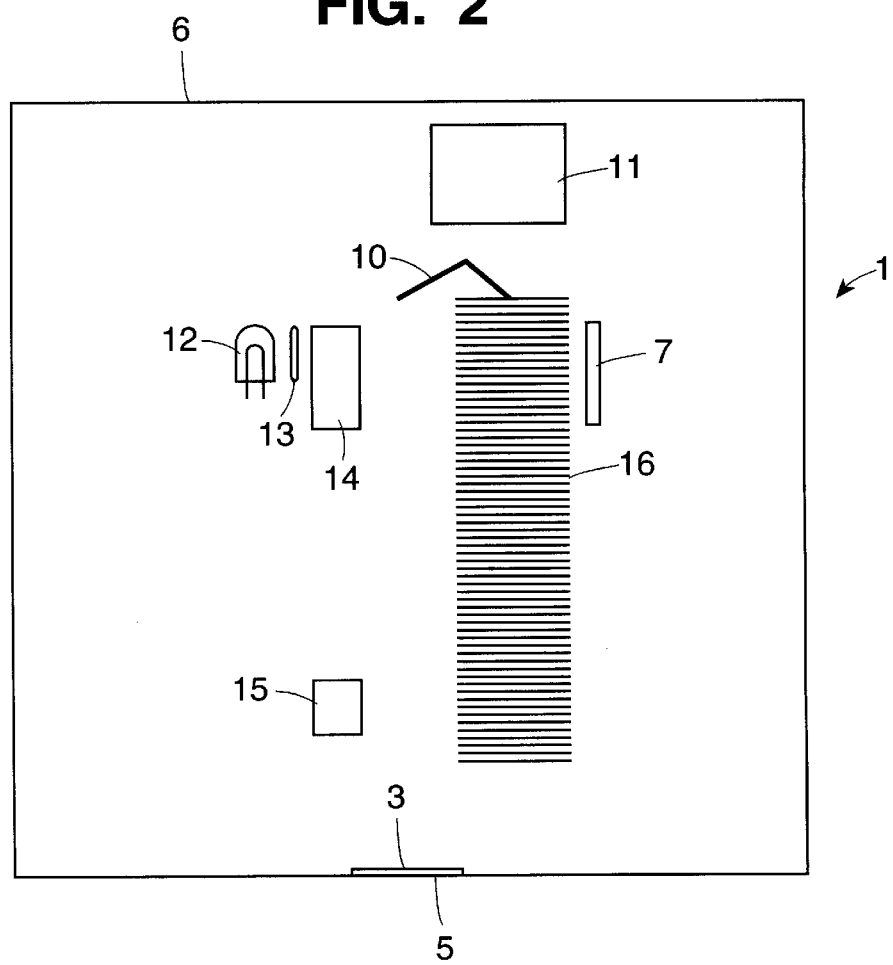
FIG. 2 is a top internal view of the analyzer depicted in FIG. 1.

FIG. 2 shows the internal details of the analyzer 1, including flap 5 at the entry/exit port 3; a bar-code reader 15 for reading read-only bar code information bar code; a photomultiplier 14 (such as the Hamamatzu R928P, commercially available from Hamamatzu Corp., Bridgewater, N.J.); interference or band pass filters 13 (such as those available commercially under part number S10-340-A from Corion Corp., Holliston, Mass.) and a light source 12, such as a xenon lamp. Conventional lenses and other known optical elements and circuitry are provided as detector 7 to obtain a desired readout signal for assaying target analyte.

At the distal end of the analyzer 1 opposite to flap 5 is located a hinged lever 10 which, when an outer edge of assay tray 30 abuts against it, serves to displace and orient conductors 16 both over and under the upper surface 35 and lower surface 34 of assay tray 30 (see FIG. 3B). Of course, lever 10 may be replaced with a pressure sensor, or proximity detecting device, etc., as desired.

Conductors 16 are of any desired material which is capable of conducting an electrical potential. Appropriate materials include metal wires, such as copper. Alternatively, the conductors 16 may be constructed with a metallic core, such a ferrous core, around which is wrapped metallic wire. Such a construction serves to increase the electromagnetic field generated, and therefore lessen the amount of energy required to operate analyzer 1.

A microprocessor 11 is provided to control the application of potential to the conductors 16. In FIGS. 5 and 6, the current carrying conductors are shown as ●; the conductors through which no potential is applied are shown as O.

Figure 5A:
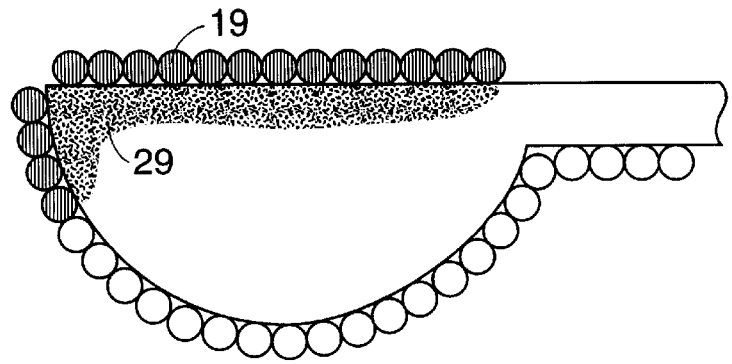
FIGS. 5A, 5B and 6A–6D are side views illustrating application of electrical potential with reference to the assay tray of FIG. 3B.
Figure 5B:
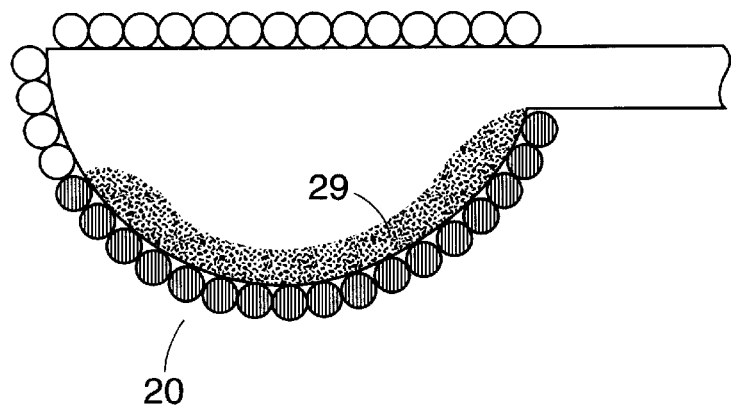
Figure 6A:
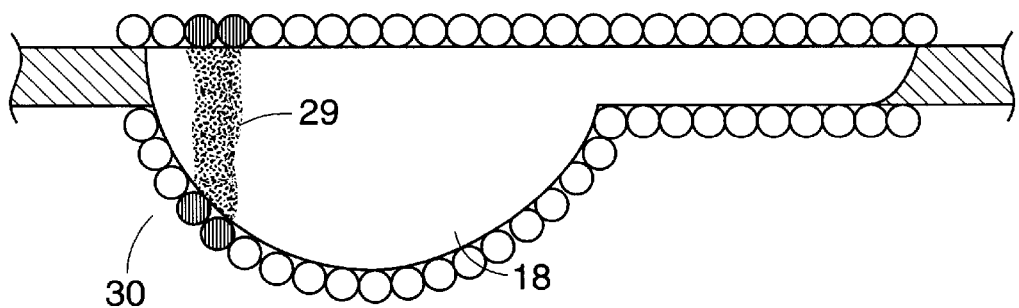
Figure 6B:
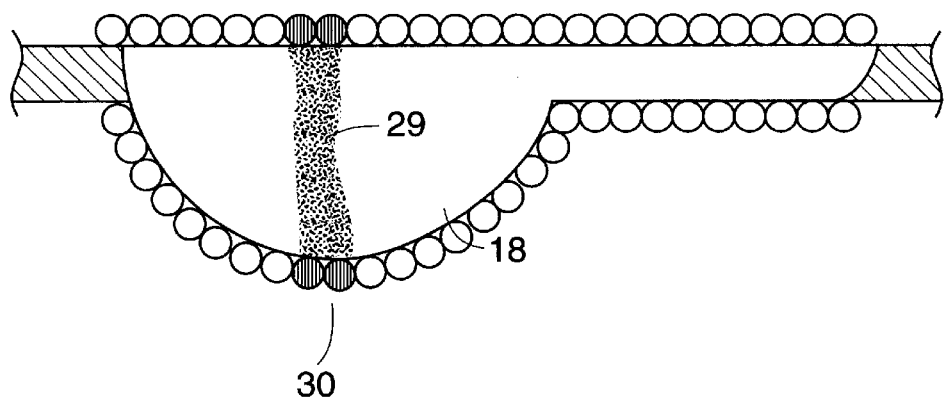
Figure 6C:
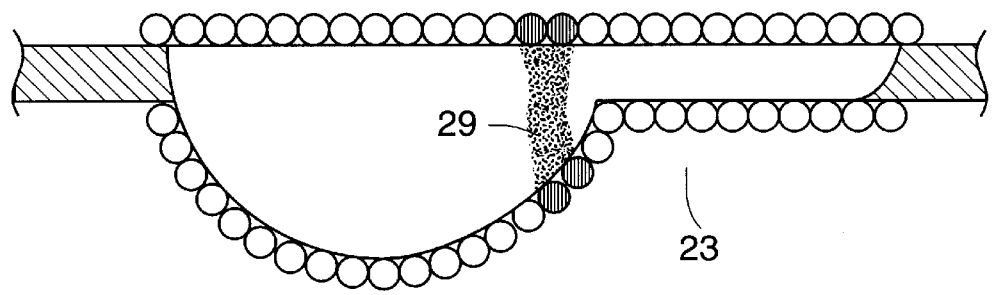
Figure 6D:
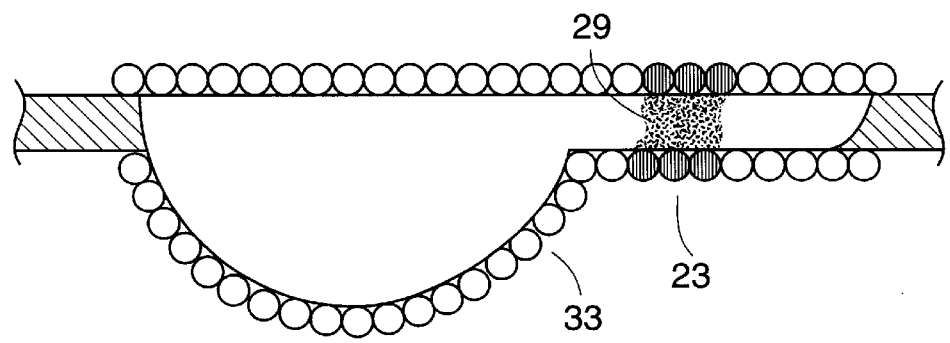

Desirably, as shown in FIGS. 5A and 5B, the applied potential is also alternated vertically between the conductors at the upper portion 19 of sample well 18 and those conductors at the lower portion 20 of sample well 18 to influence the concentrated analyte/capture agent/detector reagent complex 29 in an additional dimension. In this regard, application of potential, as illustrated in FIGS. 5 and 6 together, enhances both formation and concentration of analyte/capture agent/detector reagent complex and results in more efficient transport of the same to detection region 23.

As shown sequentially in FIGS. 6A–6D, the applied potential is cycled by the microprocessor in a horizontal wave-like manner beginning from the portion 31 of sample well 18 distal to detection region 23 concentrating and advancing any labelled analyte/capture agent complex 29 thereat (as well as all unbound magnetic capture agent) to the middle portion 32 of sample well 18 and then continuing to the portion 33 of sample well 18 proximal to detection region 23 so as to ultimately accumulate all analyte/capture agent complex within detection region 23.

Of course, it is also contemplated within the scope of the present invention to bind the capture agent to ferrous materials and to provide non-permanent electromagnets to transport the complex of target analyte, capture agent and label as illustrated in the Figures and as discussed above.

After migrating from sample well 18 into detection region 23, the presence and amount of labelled analyte/capture agent complex is determined. The labelled analyte/capture agent complex is determined using a variety of conventional detectors depending on the particular target analyte to be assayed. For instance, if the target analyte has a known characteristic absorbance spectrum, then detection region 23 may simply be illuminated with light of the appropriate wavelength. Based on this teaching and on the knowledge of those of ordinary skill in the art, those artisans will readily be able to make appropriate choices of suitable detectors.

Figure 4A:
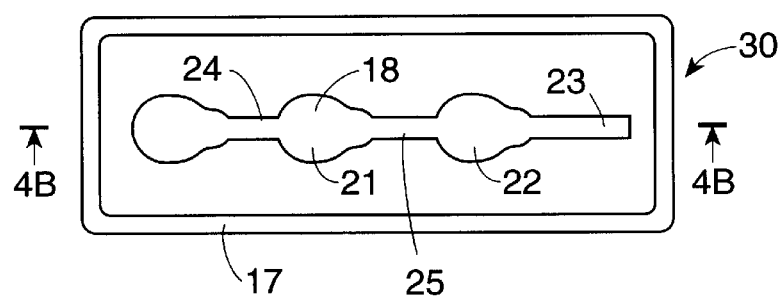
FIG. 4A is a top view of another assay tray for use with the analyzer of FIG. 1.
Figure 4B:
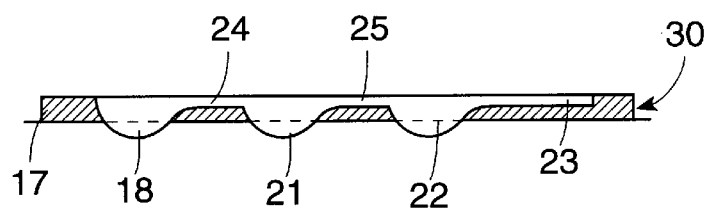
FIG. 4B is a cross-section of the assay tray depicted in FIG. 4A, taken generally along the line 4B—B.

In an alternative embodiment as shown in FIGS. 4A and 4B, instead of a single well containing both the magnetic capture agents and the detector reagent, the analyte/capture agent complex is transported via passage 24 from sample well 18 to a second well 21, which contains a label, by cycling the applied potential as described previously. Providing assay tray 30 with a detector well 21 is particularly useful when the target analyte itself is not readily detectable, e.g., where the analyte does not have a chromophore detectable in the electromagnetic spectrum, such as in the visible range.

The detector reagent provided within detector well 21 interacts selectively with the target analyte to form a labelled analyte which is capable of being detected. The detector reagent may be selected from any conventional labelling materials, provided that the detector reagent is nonmagnetic and nonferrous so that it does bind to the magnetic capture agent or otherwise caused to independently migrate to detection region 23 and thereby give inaccurate assay results.

For example, the detector reagent may be chosen from a variety of fluorescent materials, UV-active materials, materials possessing a chromophore which is detectable in the visible range of the electromagnetic spectrum, radiolabel tags, and chemiluminescent materials. In addition, suitable detector reagent may be dormant, e.g., not detectable absent interaction with the target analyte.

Preferable detector reagents will be determined readily by those of ordinary skill in this art. For instance, an appropriate detector reagent for use in an immunoassay, is an antibody probe. Similarly, an appropriate detector reagent for use in a nucleic acid assay is an oligodeoxynucleotide probe. Preferably, these probes are coupled covalently to latex particles, such as fluorescent Covaspheres® 0.5% (commercially available from Duke Scientific Corp., Palo Alto, Calif.).

In instances such as above when a fluophphore is utilized as a detector reagent, a fluorescent reader is an appropriate detector to assay the fluorescence of the labelled analyte/capture agent complex. Examples of commercially available fluorescence detectors include EG&G model SPCM-100-PQ, Hamamatzu PMT R-9288, Perkin Elmer Luminescence Spectrophotometer LS-50 and the like.

As will be understood in this alternative embodiment, the analyte/capture agent complex interacts in detector well 21 with the detector reagent thereby forming a labelled analyte/capture agent complex. The labelling reaction with the detector reagent is ordinarily carried out at a temperature of about 20° to about 45° C., preferably about 37° C., and ordinarily occurs within a period of time of about 30 seconds to about 5 minutes, preferably about 30 seconds to about one minute. Again, these reaction temperatures and times will vary within or beyond these ranges depending on the target analyte and the detector reagent chosen to label that analyte.

Assay tray 30 may also include an additional well 22 interposed via interconnection region or passage 25 between detector well 21 and detection region 23 for washing the labelled analyte/capture agent complex with wash solution. Suitable wash solutions are those materials capable of removing residual amounts of extraneous materials, such as unbound detector reagent, from the labelled analyte/capture agent complex. Examples of such wash solutions include a wash buffer containing about 10 mM of sodium phosphate at pH 7, about 0.1% of BSA (w/v), and about 0.05% of Nonidet P-40 (v/v) (commercially available from Sigma Chemicals, St. Louis, Mo.). Other wash buffers known to those of skill in the art may also be used herein.

With reference to FIG. 4A, target analyte is first bound to magnetic capture agent in well 18, labelled in well 21 and washed in well 22. Of course, it is also acceptable to first label the target analyte in well 18 prior to binding the same to magnetic capture agent in well 21 and subsequent to washing in well 22. Alternatively, the target analyte may be labelled and bound to magnetic capture agent simultaneously within one well. Similarly, in all instances, the washing step within well 22 may be omitted, if desired.

In all the above embodiments, however, it is preferable that electrical potential is applied to conductors 16 as illustrated in FIGS. 5A and 5B when the target analyte is being labelled, when the labelled target analyte is being bound to the magnetic capture agent and/or when the labelled analyte/capture agent complex is being washed, in order to accomplish more efficiently these processes.

The rate of passage of the labelled target analyte, analyte/capture agent complex and/or labelled analyte/capture agent complex within the assay tray 30 may be controlled by varying the speed at which the potential is applied to and removed from the conductors 16, as well as the magnitude of that potential, so as to optimize the conditions necessary for the particular reaction or process step sought to occur. In certain instances, accordingly, it may be advantageous to retard or accelerate the rate of passage through the device (or vary the rate of passage within various sections of the device) so as to optimize interaction time within a particular section of assay tray 30.

In another aspect of the present invention, a system is provided wherein insertion of the assay tray 30 within the analyzer 1 triggers the bar-code reader 15 to read read-only information portrayed on assay tray 30 and to transmit that information to microprocessor 11.

Based on the read-only information embodied in the bar code on the device (e.g., a serial number, an expiration date, and the type of assay to be performed), the microprocessor 11 determines the identity of the target analyte and conducts the assay. As a quality control measure, the bar code may also include an expiration date to prevent the performance of assays where the integrity of any reagents within the compartment of the device may have been compromised.

Example I

Target analyte-containing fluid is introduced into sample well 18 of assay tray 30 by dispensing with a disposable pipette. Of course, if the concentration of the target analyte is also to be determined, a predetermined volume of sample is introduced into sample well 18, or the volume of the sample that is introduced is entered into analyzer 1 via alphanumeric keypad 4.

Thereafter, assay tray 30 is inserted into analyzer 1. The magnetic capture agent contained in sample well 18 and the target analyte contained in the sample interact. This interaction is facilitated by alternating an electrical potential between the upper conductors 19 and the lower conductors 20 as shown in FIGS. 5A and 5B.

Then, microprocessor 11 controls the application of the potential through the conductors in a wave-like manner from the distal portion 31 of sample well 18 toward the proximal end 33 of sample well 18 and into interconnection region or channel 24. (See FIGS. 4A, 4B and 6A–6D.) From channel 24, the cycling of the potential is continued in the wave-like manner until the analyte/capture agent complex is introduced into detector well 21.

In detector well 21, microprocessor 11 controls the cycling of the electrical potential as illustrated in FIGS. 5A and 5B to thoroughly mix the analyte/capture agent complex with a fluorescent label. Thereafter, the labelled analyte/capture agent complex is transported through detector well 21 and interconnection region or passage 25 into wash well 22 by application of a wave-like potential to the conductors as shown in FIGS. 4A, 4B and 6A–6D. As before, microprocessor 11 then controls the cycling of applied potential as shown in FIGS. 5A and 5B in order to efficiently wash the labelled analyte/capture agent complex within wash well 22.

To reach the detection region 23, the microprocessor 11 continues the wave-like application of potential in wash well 22 to detection region 23 as shown in FIGS. 4A, 4B and 6A–6D. If desired, once within detection region 23, the labelled analyte/capture agent complex may be retained in detection region 23 by application of a continuous potential thereto.

Microprocessor 11 then commences activation of the light source 12 and the photomultiplier tube 14. The strength of the signal generated by photomultiplier 14 corresponds to the concentration of fluorescent particles in the detection region 23, which in turn is proportional to the target analyte concentration in the predetermined volume of sample fluid. The signal is then used to confirm the presence of target analyte in the sample, as well as to determine the actual target analyte concentration in the sample by plotting on a standardized curve stored in microprocessor 11.

The present invention also contemplates a kit in which a single-use, disposable assay tray 30 contains all of the necessary reagents to conduct an assay. In such a kit, it is desirable to heat-seal a thin protective laminate on the top surface of body 17 to ensure its sterility, etc. An appropriate laminate film is 0.48 mil polyester/0.75 mil Aclar [such as Aclar 88A/3 EX-23 polypropylene (commercially available from Tekni-Plex, Somerville, N.J.)]. Such material is preferably hydrophobic which, together with the surface tension of the liquid reagents disposed within the wells of the assay tray 30, minimizes undesired reagent cross-over therewithin.

While the present invention has been described herein by way of illustration, it will be clear to those of skill in the art that changes and modifications may be made from the specific description without departing from the spirit and scope of the present invention defined by the claims.

What is claimed is:

1. A device for assaying a target analyte, comprising:
   a housing comprising means for receiving a tray,
   the tray comprising at least one well and an interconnected detection region wherein the well and detection region contain a fluid,
   said well containing said target analyte, a magnetic capture agent and a label;
   input means for inputting to said device data selected from the group consisting of information identifying said target analyte, information identifying a volume of said fluid, information identifying said magnetic capture agent and information identifying said label;
   microprocessor means for applying a wave-like electrical potential for transporting a complex of said target analyte, said magnetic capture agent and said label to said detection region of said tray; and
   identification means for identifying the presence of said target analyte in said labeled complex at said detection region.

2. The device according to claim 1, wherein said tray provides said magnetic capture agent and said label in separate wells.

3. The device according to claim 1, wherein said electrical potential transports said complex through a wash buffer before reaching said detection region.

4. The device according to claims 1, wherein said microprocessor means also applies an electrical potential to displace magnetized material in a direction substantially normal to a line through said at least one well and said detection region.

5. A tray, comprising a body provided with a well and an interconnected detection region, wherein the well and detection region contain a fluid said well containing a magnetic capture agent and a label for binding to a target analyte.

6. A tray, comprising a body provided with two interconnected wells and a detection region connected to one of said wells oriented along an axis, wherein the wells and detection region contain a fluid, wherein one said wells contains a magnetic capture agent for binding to a target analyte and the other of said wells contains a label for binding to said target analyte.

7. A process for assaying a target analyte, said process comprising the steps of:
   selecting an assay tray provided with a well and an interconnected detection region wherein the well and the detection region contain a fluid, said well further containing a magnetic capture agent and a label;
   adding to said well a target analyte sample;
   causing any target analyte in said sample to form a complex with said magnetic capture agent and said label;
   applying electrical potential to said complex and transporting said complex to detection region; and
   determining the presence of said complex in said detection region.

8. The process according to claim 7, further comprising the step of determining the concentration of said complex in said detection region.

9. The process according to claim 7, wherein said magnetic capture agent and said label are provided in separate wells in said assay tray.

10. The process according to claim 9, wherein said assay tray further provides a wash well and said process further comprises washing said complex in said wash well before determining the presence of said label.

* * * * *